US008171932B2

(12) United States Patent
Rittner et al.

(10) Patent No.: US 8,171,932 B2

(45) Date of Patent: May 8, 2012

(54) OXYGEN BREATHING DEVICE FOR AN AIRCRAFT

(75) Inventors: Wolfgang Rittner, Siblin (DE); Rudiger Meckes, Berkenthin (DE); Mark Niedostatek, Wenzendorf (DE)

(73) Assignee: Intertechnique, S.A., Plaisir, Cedex (FR)

( * ) Notice: Subject to any disclaimer, the term of this patent is extended or adjusted under 35 U.S.C. 154(b) by 506 days.

(21) Appl. No.: 12/501,525

(22) Filed: Jul. 13, 2009

(65) Prior Publication Data

US 2010/0012116 A1 Jan. 21, 2010

Related U.S. Application Data

(60) Provisional application No. 61/079,836, filed on Jul. 11, 2008.

(51) Int. Cl.

| | |
|---|---|
| ***A61M 16/00*** | (2006.01) |
| ***G05B 1/00*** | (2006.01) |
| ***A62B 7/00*** | (2006.01) |
| ***A62B 7/10*** | (2006.01) |
| ***A62B 9/00*** | (2006.01) |
| ***A62B 19/00*** | (2006.01) |
| ***A62B 23/02*** | (2006.01) |

(52) U.S. Cl. ......... 128/205.27; 128/204.18; 128/205.11; 128/205.12

(58) Field of Classification Search ............. 128/202.12, 128/204.18, 205.11, 205.12, 205.26, 205.27, 128/205.28; 454/71–74; 244/118.5; 95/128, 95/138; 96/108, 113, 116, 127, 128, 142; 422/122, 123, 305; *A61M 16/00; G05B 1/00; A62B 7/00, 9/00, 19/00, 23/02*

See application file for complete search history.

(56) References Cited

U.S. PATENT DOCUMENTS 3,981,300 A 9/1976 Williams (Continued)

FOREIGN PATENT DOCUMENTS

EP 1504782 2/2005

(Continued)

*Primary Examiner* — Oren Ginsberg

(74) *Attorney, Agent, or Firm* — Dean W. Russell; Kilpatrick Townsend & Stockton LLP

(57) ABSTRACT

The invention relates to an oxygen breathing device for an aircraft, in particular for oxygen supply to crew member in a cockpit of an aircraft, comprising a filter unit having an inflow port and an outflow port, the filter unit being adapted to extract nitrogen from an air flow flowing from the inflow port to the outflow port through the filter unit, wherein the filter unit is adapted to receive compressed air, preferably, bleed air from a precompressor stage of a turbine driving the aircraft, or directly by a separate electrically driven compressor, via a bleed air supply line connected to the inflow port, a first pressure regulator in the bleed air supply line, a first water separator which is arranged in the bleed air supply line in flow direction of the bleed air before the first pressure regulator and a connection port which can be brought in fluid communication with said outflow port of the filter unit and which is adapted to be coupled to at least one oxygen supply mask via an oxygen supply line. According to the invention, a chemical oxygen generator comprising at least one substance adapted to produce oxygen in a chemical reaction and to provide said oxygen to an outflow port of said oxygen generator is provided. The outflow port of said chemical oxygen generator is connected to an auxiliary oxygen supply line and a control unit is adapted to selectively provide oxygen from the filter unit or the chemical oxygen generator to an oxygen supply mask coupled to the connection port.

9 Claims, 1 Drawing Sheet

U.S. PATENT DOCUMENTS

| | | | | |
|---|---|---|---|---|
| 4,651,728 | A * | 3/1987 | Gupta et al. | 128/201.28 |
| 4,681,602 | A * | 7/1987 | Glenn et al. | 95/47 |
| 5,199,423 | A * | 4/1993 | Harral et al. | 128/202.26 |
| 5,858,063 | A | 1/1999 | Cao et al. | |
| 6,997,970 | B2 * | 2/2006 | Crome | 95/8 |
| 2003/0233936 | A1 | 12/2003 | Crome | |
| 2004/0244585 | A1 | 12/2004 | Meckes et al. | |
| 2005/0028868 | A1 | 2/2005 | Basset et al. | |
| 2010/0043794 | A1 * | 2/2010 | Saito et al. | 128/204.22 |

FOREIGN PATENT DOCUMENTS

| | | |
|---|---|---|
| FR | 2855145 | 11/2004 |

* cited by examiner

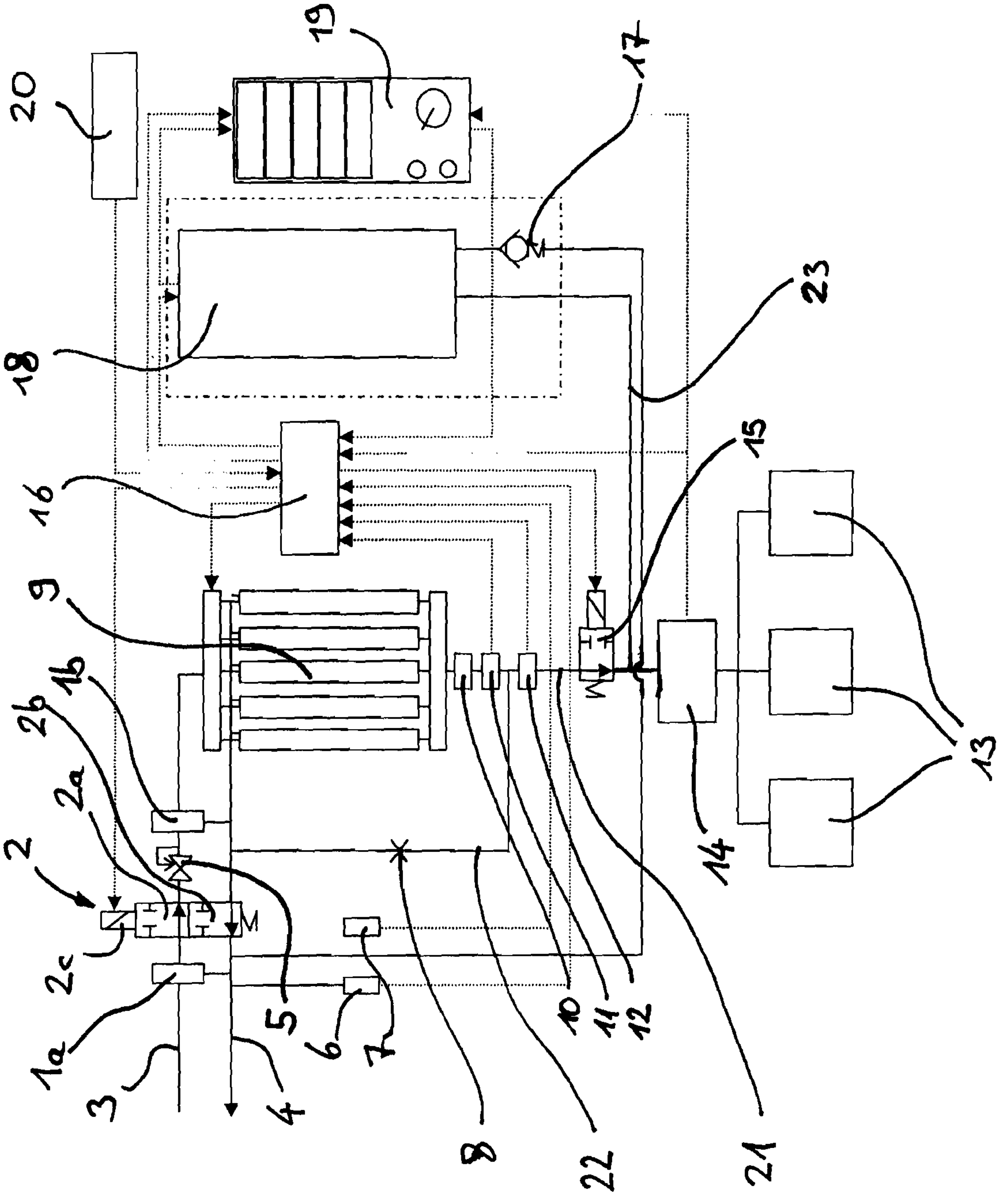
20
19
17
18
23
16
15
9
1b
2b
2a
2
2c
1a
3
4
5
6
7
M
8
22
10
11
12
21
14
13

OXYGEN BREATHING DEVICE FOR AN AIRCRAFT

CROSS REFERENCE TO RELATED APPLICATION

This application claims the benefit of U.S. Provisional Application No. 61/079,836 filed on Jul. 11, 2008, the entire contents of which are incorporated herein by reference.

BACKGROUND

The invention relates to an oxygen breathing device for an aircraft, in particular for oxygen supply to crew member in a cockpit of an aircraft, comprising a filter unit having an inflow port and an outflow port, the filter unit being adapted to extract nitrogen from an air flow flowing from the inflow port to the outflow port through the filter unit, wherein the filter unit is adapted to receive compressed air, preferably, bleed air from a precompressor stage of a turbine driving the aircraft, or directly by a separate electrically driven compressor, via a bleed air supply line connected to the inflow port, a first pressure regulator in the bleed air supply line, a first water separator which is arranged in the bleed air supply line in flow direction of the bleed air before the first pressure regulator and a connection port which can be brought in fluid communication with said outflow port of the filter unit and which is adapted to be coupled to at least one oxygen supply mask via an oxygen supply line.

FIELD OF THE INVENTION

Such oxygen breathing devices are referred to as OBOGS (on-board oxygen generating system) and are able to continuously provide oxygen to a crew member of an aircraft. To achieve this, such oxygen breathing devices usually receive pressurized outside air from a precompressor stage of in particular a turbine driving the aircraft. Said bleed air is directed through the filter unit which comprises a number of sieve beds and is adapted to effect an enrichment of oxygen in the bleed air by filtering nitrogen out of the bleed air. By this, an airflow comprising a high concentration of oxygen can be provided to the crew member to permanently supply the crew member with oxygen in flight condition.

A first problem associated with such oxygen breathing devices is the need to replace the filter unit after a certain period of service. This is required because the effectiveness of the filter unit to filter nitrogen decreases significantly over time of service. This results in a low economical efficiency of such oxygen breathing devices. This is the main reason why oxygen breathing devices as described above are only used in military aircraft applications.

Usually, the proper functioning of such oxygen breathing devices can be monitored by measuring oxygen concentration and pressure in the line supplying the oxygen to the oxygen mask. However, such monitoring method is not sufficient in applications where the oxygen breathing device is not permanently in use. A further problem associated with such oxygen breathing devices thus is the need to monitor proper functioning of the device in a non-use situation.

Still further, there is a need for an oxygen breathing device wherein in case of failure of the oxygen supply from the bleed air supply line via the filter unit a proper oxygen supply to the crew member using the oxygen breathing device is maintained.

The problem is solved by an oxygen breathing device further comprising a chemical oxygen generator comprising at least one substance adapted to produce oxygen in a chemical reaction and to provide said oxygen to an outflow port of said oxygen generator, a starter adapted to start said chemical reaction upon receipt of a start signal, preferably an electrical start signal, wherein the outflow port of said chemical oxygen generator is connected to an auxiliary oxygen supply line and a control unit adapted to selectively provide oxygen from the filter unit or the chemical oxygen generator to an oxygen supply mask coupled to the connection port.

SUMMARY OF THE INVENTION

According to the invention, an auxiliary, completely independent and technically completely different second source for oxygen generation is provided in the oxygen breathing device. Thus, an oxygen breathing device is provided comprising a main oxygen supply system and an independent auxiliary oxygen supply system. By this, in case of failure of the bleed air supplied or the filter unit or any other important unit within the oxygen breathing device producing breathing air from bleed air, the auxiliary oxygen generation can be initiated and the user can safely be provided with oxygen hereafter. According to the invention, a chemical oxygen generator is used for such auxiliary oxygen generation wherein at least one substance is stored which can be started by a starter to produce oxygen. Such chemical oxygen generator may comprise one, two or more reaction substances which are able to perform a chemical reaction upon receipt of a starting signal like e.g. an electrical or thermal starting signal or an injection of a specific reactive substance to produce oxygen.

According to the invention, it is possible to provide oxygen by the auxiliary oxygen supply system in a very similar concentration and pressure range like provided by the main oxygen supply system. Thus, no further steps have to be undertaken to adapt the oxygen produced by the auxiliary system before providing it to the user of the oxygen breathing device.

According to a first preferred embodiment, the oxygen breathing device comprises a shut-off valve to interrupt flow through the bleed air supply line, the shut off valve being preferably arranged in bleed air flow direction between the first water separator and the first pressure regulator. By this, it is possible to pneumatically seal the whole oxygen breathing device in terms of non-use or in a switched-off situation.

Still further, the shut off valve may preferably comprise a first valve unit adapted to interrupt the flow through the bleed air supply line and a second valve unit adapted to interrupt flow through a vent line connecting the filter unit with ambient pressure, wherein the first valve unit is adapted to be switched between a first condition wherein the flow through the bleed air supply line and the flow through the vent line is open and a second position wherein the flow through the bleed air supply line and the flow through the vent line is shut. With this embodiment it is possible to pneumatically seal the whole oxygen breathing device. This will further extend the lifetime of the filter unit as it is neither in flow communication with the bleed air line and the vent line nor under bleed air pressure in times of non-use which may be achieved by additional valve means or a short time delay between closing of the two valve units.

According to a still further preferred embodiment, a pressure sensor and an oxygen sensor is comprised in the oxygen breathing device, wherein the pressure sensor and the oxygen sensor are arranged in the oxygen supply line and the control unit is adapted to monitor the signals of the pressure sensor and the oxygen sensor and to provide an output signal indicating proper function of the oxygen breathing device, in particular to provide such output signal after a certain predetermined time period has elapsed after the pressure sensor signal had reached a predetermined limit and the oxygen sensor signal has reached a predetermined limit. This preferred embodiment is particularly helpful for monitoring proper functioning of the breathing device after switching on. The absolute content of oxygen in the breathing air depends on the concentration of oxygen in the breathing air and the pressure of the breathing air. Thus, a reliant determination of the oxygen content is only possible if a certain pressure level is achieved and maintained or permanently monitored. To provide such reliant oxygen content measurement, the pressure of the breathing air is monitored in the oxygen supply line and if this pressure level has reached or exceeded a certain predetermined level, a short time delay starts and after this time delay has elapsed the oxygen concentration is measured via the oxygen sensor. By this, the oxygen content in the oxygen supply line can be determined in a safe manner since pressure is likely to be constant during oxygen measurement. It is to be understood, that both sensors are arranged in flow direction behind the filter unit. Preferably, the pressure sensor is arranged in flow direction behind the oxygen sensor.

According to a further preferred embodiment, the oxygen breathing device comprises a monitor line connecting the outflow port of the filter unit to a calibrated orifice and allowing a permanent small oxygen flow through an oxygen sensor, wherein the oxygen sensor monitors the oxygen concentration of the permanent small oxygen flow and outputs an oxygen concentration signal to the control unit, said control unit comparing said oxygen signal to a predetermined value and putting out a signal of proper function or malfunction of the oxygen breathing device, and the monitor line is connected to the oxygen supply line in flow direction before the pressure sensor and behind the oxygen sensor. This preferred embodiment specifically addresses the problem of how to monitor an oxygen breathing device in times of non-use. In particular in systems wherein the oxygen breathing device is not in permanent use by the user it is important to allow for such monitoring in a non-use condition of the device. This will allow to put out a signal of proper functioning of the device or to alternatively request exchange of the system or parts of it or to indicate the user to switch to another breathing device. According to the invention, a permanent minimum flow of bleed air is provided through the system by providing a calibrated orifice having a very small cross-section and allowing the breathing air to exit to ambient pressure. In this context, ambient pressure is to be understood as the pressure in the space wherein the user of the oxygen breathing device is present which may be a cabin under pressure like e.g. in case of an oxygen breathing device for the use by a crew member of an aircraft. The small flow of breathing air through the orifice allows to monitor oxygen content in flow direction behind the filter unit by the oxygen sensor and to thus output a signal of proper function or malfunction of the oxygen breathing device. It is to be understood that preferably an oxygen sensor and a pressure sensor, as described above, is provided to allow for enhanced monitoring of the function of the system. In such case, the oxygen sensor must be arranged within the flow of oxygen whereas the pressure sensor can be in fluid communication of this flow of the breathing air from the filter unit to the calibrated orifice but does not require flow through the pressure sensor itself.

According to a further preferred embodiment, the oxygen breathing device is improved by a second water separator which is arranged in the bleed air supply line between the first pressure regulator and the inflow port of the filter unit.

While it was formerly known to provide a water separator in front of the first pressure regulator to prevent introduction of liquid water into the whole system at the bleed air inlet of the whole oxygen breathing system, according to this preferred embodiment, two water separators are provided whereby the first is arranged before the pressure regulator and the second is provided behind the pressure regulator. By this, a significant amount of free water in the bleed air can be extracted by the first water separator. Additional water which is precipitated after temperature decrease in the pressure regulator is extracted in the second water separator. Although this water usually is not present in the air provided to the user because in the course of further processing of the bleed air in the system this water is stored in hygroscopical parts of the filter unit and is volatilized following temperature increase, the second water separator significantly extends the maintenance period or the time of the need for replacement of the filter unit since the enrichment of the hygroscopical sieve beds within the filter unit with water significantly reduces the lifetime of the filter unit.

According to a further preferred embodiment, the oxygen breathing device is further improved by comprising an oxygen sensor monitoring the oxygen flow to the connection port of the oxygen breathing device, the oxygen sensor being connected to the control unit, wherein the control unit is adapted to compare the oxygen sensor signal to a predetermined desired minimum oxygen level and to activate the starter of the chemical oxygen generator if the oxygen flow falls below said level. It is to be understood that this oxygen sensor can be the same oxygen sensor as described above for other preferred embodiments or can be an independent oxygen sensor. The provision of such oxygen sensor connected to the control unit allows a permanent monitoring of the oxygen flow and an activation of the auxiliary oxygen supply system in case that the signal of the oxygen sensor signalizes that the oxygen flow has fallen below a predetermined minimum level. By this, an automatic activation of the chemical oxygen generator can be produced to prevent an interruption of the oxygen supply to the user in the course of failure of the main oxygen supply system. In particular, said control unit can start the chemical reaction within the chemical oxygen generator via the starter and may additionally switch an oxygen source select valve a certain time period after said start to allow for sufficient oxygen generation within the chemical oxygen generator. In most cases of failure of an oxygen supply system based on bleed air and a filter unit the oxygen flow will not fall under a predetermined level in a sudden change but will rather slowly fall below the predetermined level. In such cases, it is not required to immediately switch to an alternative oxygen supply system but the oxygen flow via the main system can be maintained for a certain period of time after the decrease of oxygen flow was detected.

According to a still further preferred embodiment, at least one oxygen mask and a box for storing said oxygen mask is provided, wherein a switch is arranged at the box, the switch being coupled to a control unit to activate oxygen supply if the oxygen mask is taken out of the box. By this, it is possible to store the oxygen mask in a non-use situation in a box where it is to be understood that the box could include a hook, a frame or the like adapted to take up the oxygen mask in a hanging or lying position. In case that the oxygen mask is stored in said box, a switch is provided in that box which is arranged such that it is activated as soon as the oxygen mask is stored in the box. By this, the switch coupled to said control unit can deactivate oxygen flow as soon as the oxygen mask is put into the box and the control unit can activate the oxygen flow as soon as the mask is taken out of the box.

Further, a pneumatically sealing of the oxygen breathing device can be activated or deactivated by putting the oxygen mask out of the box or into the box, as described beforehand.

Finally, a still further preferred embodiment may comprise an oxygen source select valve, said oxygen source select valve being arranged to selectively provide oxygen from said oxygen filter unit or from said chemical oxygen generator to said connection port.

The oxygen source select valve may be a shut-off valve in the oxygen supply line arranged in flow direction before a coupling of the auxiliary oxygen supply line to said oxygen supply line. By this, shutting off the flow coming from the filter unit will allow to provide oxygen from the chemical oxygen generator. The oxygen source select valve may alternatively comprise a first input port coupled to said chemical oxygen generator via said auxiliary oxygen supply line, a second input port coupled to said oxygen filter unit via said oxygen supply line and an output port in fluid communication with said connection port, wherein the oxygen source select valve is adapted to selectively provide oxygen from the first input port or from the second input port to the output port. This oxygen source select valve can be automatically activated in case of failure of the main system to switch to oxygen supply from the auxiliary system by a control unit which may at the same time start the chemical oxygen generator via the starter to produce oxygen. The oxygen source select valve may be further adapted to automatically switch back to the main oxygen supply via the bleed air and the filter unit in case that the failure of this main supply is overcome. Alternatively or additionally the oxygen source select valve may allow manual selection of the oxygen source.

BRIEF DESCRIPTION OF THE DRAWING

A preferred embodiment of the invention is described referring the FIGURE.

In the FIGURE, a schematical set-up of an oxygen breathing device according to a preferred embodiment of the invention is shown.

DETAILED DESCRIPTION

The oxygen breathing device shown in the FIGURE is connected to a precompressor stage of a turbine driving the aircraft or another source of compressed air via a bleed air supply line 3. The bleed air supply line 3 is directly coupled to a first water separator 1*a* wherein water is extracted from the bleed air.

A bifunctional and automatically activated shut-off valve 2 is arranged in the bleed air supply line 3 in flow direction behind the first water separator 1*a*. The shut-off valve 2 comprises a first valve unit 2*a* which is adapted to open or to shut off the flow from the bleed air source to a filter unit 9. The second valve unit 2*b* is adapted to open or shut off the flow through a vent line 4 from the filter unit 9 to ambient air. An electromechanical actuator 2*c* is coupled to the two valve units 2*a*, 2*b* to provide for two distinct valve positions. In the first position, the flow through the bleed air supply line 3 is opened and the flow through the vent line is opened; in the second position, the flow through the bleed air supply line 3 is shut and the flow through the vent line 4 is shut.

In the bleed air supply line between the shut-off valve 2 and the filter unit 9 a second water separator 1*b* is arranged to extract water which precipitated in the course of pressure decrease of the bleed air in a pressure regulator 5 arranged between the shut-off valve 2 and the second water separator 1*b*.

The filter unit 9 comprises a plurality of sieve beds which extract nitrogen from the bleed air flowing through the bleed air supply line 3. In flow direction behind these sieve beds a gas outlet filter 10 is arranged in an oxygen supply line 21. In flow direction behind the gas outlet filter an oxygen sensor 11 and a pressure sensor 12 is arranged. The oxygen sensor 11 is arranged in flow direction before the pressure sensor 12. Between the oxygen sensor 11 and the pressure sensor 12 a monitoring line 22 is branched off which is coupled to the venting line 4 via a calibrated orifice 8.

Further, in flow direction behind the pressure sensor 12 an oxygen source select valve 15 is arranged in the oxygen supply line 21.

In flow direction behind the oxygen source select valve 15 a low pressure switch 14 is arranged in the oxygen supply line which is connected to a plurality of cockpit masks 13.

Between the oxygen source select valve 15 and the low pressure switch 14 an auxiliary oxygen supply line 23 is coupled to the oxygen supply line 21. The auxiliary oxygen supply line 23 is coupled to the low pressure switch and cockpit masks 13 to a chemical oxygen generator 18 comprising a starter (not shown). The chemical oxygen generator 18 is further coupled to the vent line 4 via a pressure limitation valve 17.

An electronic control unit 16 is provided receiving signals from the oxygen sensor 11, the pressure sensor 12, an altitude pressure sensor 6 and a cabin pressure sensor 7. Further, signals from the low pressure switch 14, an altitude pressure switch 20 and a pilot control panel 19 are input into the electronic control unit 16. The control unit is adapted to activate the shut-off valve 2, the oxygen source select valve 15 and the starter of the chemical oxygen generator 18. Further, the electronic control unit 16 provides signals to the pilot control panel 19 to signalize the status of the oxygen supply via the bleed air line 3 and the oxygen supply line 21 and via the chemical oxygen generator 18 and the auxiliary oxygen supply line 23.

The oxygen breathing device according to the invention will work as follows:

In system start upon aircraft system power up the electronic control unit 16 will be supplied with electrical power and the cycling of the sieve beds within the filter unit 9 starts. The filter unit 9 will be supplied with pressurized bleed air via the bleed air supply line 3. The shut-off valve 2 and the oxygen source select valve 15 will be activated and thus opened and the bleed air flows through the first water separator 1*a*, the pressure regulator 5 and the second water separator 1*b* into the filter unit 9. As soon as the pressure sensor 11 receives sufficient pressure a timer within the electronic control unit 16 will provide a time delay to guarantee for a good stabilized oxygen sensor 12 signal. Venting of the sieve beds of the filter unit 9 will be through the vent line 4 to the outside of the aircraft. The altitude pressure sensor 6 monitors the aircraft altitude. The signal of the altitude pressure sensor 6 will be provided to the electronic control unit 16 to optimize the cycle time of a rotary valve included in the filter unit 9. This rotary valve serves to pressurize the molecular sieve beds for adsorption of nitrogen and depressurize the molecular sieve beds for desorption of nitrogen in a cyclic manner. After warm-up of the filter unit 9 the oxygen source select valve 15 at the outlet of the filter unit 9 will be activated to check the correct valve function. Continuity measurement of the electrical starter comprised in the chemical oxygen generator 18 provides the built-in test of the electrical starter and thus the chemical oxygen generator 18.

A small bleed flow at the outlet of the filter unit 9 through the monitoring line 22 and the calibrated orifice 8 will be monitored with the pressure sensor 12 and the oxygen partial pressure sensor 11. The signals of said both sensors 11, 12 will be provided to the electronic control unit and used therein to calculate the oxygen concentration. The oxygen concentration and the product gas pressure will be used to verify the correct function of the filter unit. The filter unit status signals will be sent to the pilot control panel 19.

In pre-flight check, as soon as the aircraft system including bleed air system has been activated, sufficient flow and pressure will be available to the cockpit masks 13. This will enable the pilots to perform the cockpit mask pre-flight check, regulator tests, including mask harness inflation.

Under normal flight operation the oxygen breathing device is in stand-by mode and can be utilized whenever necessary without further warm-up needed. The continuous built-in test feature monitors the oxygen performance of the filter unit and the electronic control unit generates a system status signal "good" or "bad" which will be sent to the cockpit control panel 19.

During flight, the pilots can use the pilot masks 13 to perform pre-breathing with air provided by the oxygen breathing device at any time.

If a failure of the oxygen supply via the bleed air supply line 3 and the filter unit 9 occurs either during pre-breathing or in "in duty" mode, the electronic control unit sends a "filter failure" signal to the cockpit control panel. The electronic control unit may automatically activate the starter in the chemical oxygen generator 18 and oxygen will be provided via the auxiliary oxygen supply line 23 to the cockpit masks 13 if the masks are in use. At the same time, the oxygen source select valve 15 will be shut by the electronic control unit 16 to stop air flow from the filter unit 9 to the cockpit masks 13. As soon as the filter unit returns to good operation, the electronic control unit sends the signal "filter normal" to the cockpit control panel 19. If the filter system does not recover to a good performance, the cockpit control panel will remain in "filter failure" status. In case of a decompression or when manually selected by the pilot, the electronic control unit shuts off the filter unit outlet and activates the chemical oxygen generator 18.

In case of smoke in the cockpit the pilots can use the pilot masks to breathe through the cockpit masks.

In a decompression situation the altitude pressure switch 20 provides a signal to the electronic control unit 16 and a warning signal to the cockpit. In case of decompression, the pilots use the pilot masks 13 and will be supplied with oxygen enriched air delivered by the filter unit 9.

In case of failure of the oxygen supply via the bleed air line 3 during decompression, the electronic control unit having received the decompression signal from the altitude pressure switch 20 will automatically switch over to the chemical oxygen generator 18. As soon as the chemical oxygen generator 18 has been depleted, after the emergency descent to safe altitude, a low pressure switch 14 detects a low pressure in the supply line to the cockpit masks 13. The electronic control unit 16 switches the oxygen source select valve 15 to open to supply oxygen from the filter unit 9, even at low oxygen concentrations, to continuous supply breathing air to the pilot and thus allowing to inflate the harnesses of the cockpit masks if the pilots want to use the masks.

The invention claimed is:

1. Oxygen breathing device for an aircraft, in particular for oxygen supply to crew member in a cockpit of the aircraft, comprising:

a filter unit having an inflow port and an outflow port, the filter unit being adapted to extract nitrogen from an air flow flowing from the inflow port to the outflow port through the filter unit, wherein the filter unit is adapted to receive compressed bleed air via a bleed air supply line from a precompressor stage of a turbine driving the aircraft connected to the inflow port, or directly by a separate electrically driven compressor, a first pressure regulator in the bleed air supply line a first water separator which is arranged in the bleed air supply line in flow direction of the bleed air before the first pressure regulator, a connection port which can be brought in fluid communication with said outflow port of the filter unit and which is adapted to be coupled to at least one oxygen supply mask via an oxygen supply line, wherein:

a chemical oxygen generator comprising at least one substance adapted to produce oxygen in a chemical reaction and to provide said oxygen to an outflow port of said oxygen generator, a starter adapted to start said chemical reaction upon receipt of a start signal, preferably an electrical start signal, wherein the outflow port of said chemical oxygen generator is connected to an auxiliary oxygen supply line, a control unit adapted to selectively provide oxygen from the filter unit or the chemical oxygen generator to the at least one oxygen supply mask coupled to the connection port.

2. The oxygen breathing device according to claim 1, further comprising a shut off valve to interrupt flow through the bleed air supply line, the shut off valve being preferably arranged in bleed air flow direction between the first water separator and the first pressure regulator.

3. The oxygen breathing device according to claim 2, wherein the shut off valve comprises a first valve unit adapted to interrupt the flow through the bleed air supply line and a second valve unit adapted to interrupt flow through a vent line connecting the filter unit with ambient pressure, wherein the first valve unit is adapted to be switched between a first condition wherein the flow through the bleed air supply line is open and the flow through the vent line is open and a second position wherein the flow through the bleed air supply line is shut and the flow through the vent line is shut.

4. The oxygen breathing device according to claim 1, further comprising a pressure sensor and an oxygen sensor, wherein the pressure sensor and the oxygen sensor are arranged in the oxygen supply line and the control unit is adapted to monitor signals of the pressure sensor and the oxygen sensor and to provide an output signal indicating proper function of the oxygen breathing device, in particular to provide such output signal after a certain predetermined time period has elapsed after the pressure sensor signal had reached a predetermined limit and the oxygen sensor signal has reached a predetermined limit.

5. The oxygen breathing device according to claim 4, further comprising a monitor line connecting the outflow port of the filter unit to a calibrated orifice and allowing a permanent small oxygen flow through the oxygen sensor, wherein the oxygen sensor monitors the oxygen concentration of the permanent small oxygen flow and outputs an oxygen signal to the control unit, said control unit comparing said oxygen signal to a predetermined value and putting out a signal of proper function or malfunction of the oxygen breathing device, wherein the monitor line is connected to the oxygen supply line in flow direction before the pressure sensor and behind the oxygen sensor.

6. The oxygen breathing device according to claim 1, further comprising a second water separator which is arranged in the bleed air supply line between the first pressure regulator and the inflow port of the filter unit.

7. The oxygen breathing device according to claim 1, further comprising an oxygen sensor monitoring the oxygen flow to the connection port of the oxygen breathing device, the oxygen sensor being connected to the control unit, wherein the control unit is adapted to compare an oxygen sensor signal to a predetermined desired minimum oxygen level and to activate the starter of the chemical oxygen generator if the oxygen flow falls below said level.

8. The oxygen breathing device according to claim 1, further comprising and a box for storing the at least one oxygen mask, wherein a switch is arranged at the box the switch being coupled to the control unit to activate oxygen supply if the at least one oxygen mask is taken out of the box.

9. The oxygen breathing device according to claim 1, further comprising an oxygen source select valve, said oxygen source select valve comprising a first input port coupled to said chemical oxygen generator via said auxiliary oxygen supply line, a second input port coupled to said filter unit via said oxygen supply line and an output port in fluid communication with said connection port, wherein the oxygen source select valve is adapted to selectively provide oxygen from the first input port or from the second input port to the output port.

* * * * *